United States Patent
Hsu et al.

(10) Patent No.: US 9,556,282 B2
(45) Date of Patent: Jan. 31, 2017

(54) MODIFIED CELLULOSE AND COMPOSITE MATERIAL USING THE SAME

(71) Applicant: INDUSTRIAL TECHNOLOGY RESEARCH INSTITUTE, Hsinchu (TW)

(72) Inventors: Yu-Ying Hsu, Taichung (TW); Te-Yi Chang, Taoyuan (TW); Ju-Feng Liao, Zhubei (TW); Sheng-Ju Liao, Hsinchu (TW); Yao-Jheng Huang, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/965,264

(22) Filed: Dec. 10, 2015

(65) Prior Publication Data

US 2016/0185878 A1    Jun. 30, 2016

(30) Foreign Application Priority Data

Dec. 29, 2014 (TW) .............................. 103146047 A

(51) Int. Cl.
| | |
|---|---|
| C08B 3/10 | (2006.01) |
| C08G 81/02 | (2006.01) |
| C08B 3/12 | (2006.01) |
| C08L 1/10 | (2006.01) |
| C08L 23/10 | (2006.01) |

(Continued)

(52) U.S. Cl.
CPC . C08B 3/10 (2013.01); C08B 3/12 (2013.01); C08G 81/02 (2013.01); C08L 1/10 (2013.01); C08L 23/10 (2013.01); C07H 15/04 (2013.01); C07H 15/10 (2013.01); C07H 15/20 (2013.01); C08G 81/024 (2013.01); C08L 23/12 (2013.01)

(58) Field of Classification Search
CPC ......... C07H 15/04; C07H 15/10; C07H 15/20; C08B 3/10; C08G 81/024; C08L 1/10; C08L 23/12
See application file for complete search history.

(56) References Cited

U.S. PATENT DOCUMENTS 4,277,247 A   7/1981 Keller et al.
4,789,715 A  12/1988 Bieringer et al.
(Continued)

FOREIGN PATENT DOCUMENTS

CN   100488985 C   5/2009
CN   102099404 A   6/2011
(Continued)

OTHER PUBLICATIONS

Wang, P. and Tao, B. Y., "Synthesis of Cellulose-Fatty Acid Esters for Use as Biodegradable Plastics", Journal of Environmental Polymer Degradation 1995, 3(2), 115-119.*

(Continued)

*Primary Examiner* — Richard A Huhn
(74) *Attorney, Agent, or Firm* — Birch, Stewart, Kolasch & Birch, LLP

(57) ABSTRACT

A modified cellulose is provided. The modified cellulose is represented by the chemical formula (1):

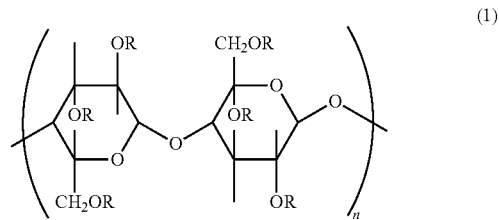

(1)

wherein n is between 60 and 2500, at least one R is selected from one of the group consisting of

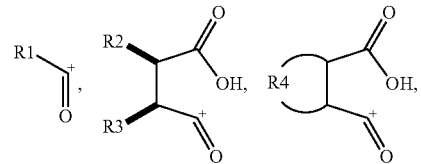

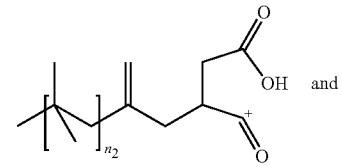 and

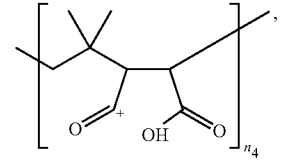

R1 is $C_{11}$ to $C_{32}$ alkyl group or $C_{11}$ to $C_{32}$ alkenyl group, R2 is hydrogen, $C_3$ to $C_{29}$ alkyl group or $C_3$ to $C_{29}$ alkenyl group, R3 is $C_3$ to $C_{29}$ alkyl group or $C_3$ to $C_{29}$ alkenyl group, R4 is $C_4$ to $C_8$ cycloalkyl group or $C_4$ to $C_8$ cycloalkenyl group, $n_2$ is between 15 and 33, $n_4$ is between 20 and 40.

16 Claims, No Drawings

(51) Int. Cl.
 C07H 15/20 (2006.01)
 C08L 23/12 (2006.01)
 C07H 15/10 (2006.01)
 C07H 15/04 (2006.01)

(56) References Cited

U.S. PATENT DOCUMENTS

| | | |
|---|---|---|
| 5,238,978 A | 8/1993 | Stein |
| 5,360,689 A | 11/1994 | Hou et al. |
| 5,750,677 A | 5/1998 | Edgar et al. |
| 5,770,726 A | 6/1998 | Kuo et al. |
| 5,929,229 A | 7/1999 | Edgar et al. |
| 6,019,925 A | 2/2000 | Diamantoglou et al. |
| 6,042,847 A | 3/2000 | Kerč et al. |
| 6,066,278 A | 5/2000 | Got et al. |
| 6,160,111 A | 12/2000 | Edgar |
| 7,749,578 B2 | 7/2010 | Oka et al. |
| 8,030,375 B2 | 10/2011 | Yano et al. |
| 8,158,777 B2 | 4/2012 | Buchanan et al. |
| 8,377,528 B2 | 2/2013 | Kyle et al. |
| 8,524,887 B2 | 9/2013 | Buchanan et al. |
| 8,591,934 B2 | 11/2013 | Hossainy et al. |
| 2004/0127614 A1 | 7/2004 | Jiang et al. |
| 2008/0194807 A1 | 8/2008 | Buchanan et al. |
| 2009/0203900 A1 | 8/2009 | Buchanan et al. |
| 2011/0160658 A1 | 6/2011 | Wang |
| 2012/0121830 A1 | 5/2012 | Buchanan et al. |
| 2012/0238741 A1 | 9/2012 | Buchanan et al. |
| 2013/0116425 A1 | 5/2013 | Buchanan et al. |
| 2013/0180173 A1 | 7/2013 | Caspar et al. |
| 2014/0079743 A1 | 3/2014 | Hossainy et al. |

FOREIGN PATENT DOCUMENTS

| | | |
|---|---|---|
| CN | 102152589 A | 8/2011 |
| CN | 102382374 A | 3/2012 |
| CN | 103459428 A | 12/2013 |
| CN | 103481838 A | 1/2014 |
| JP | 5496435 B2 | 5/2014 |
| TW | I247775 B | 1/2006 |

OTHER PUBLICATIONS

Bledzki et al., "Composites reinforced with cellulose based fibres", Elsevier, Progress in Polymer Science, 1999, vol. 24, pp. 221-274.

Iwamoto et al., "Mechanical properties of polypropylene composites reinforced by surface-coated microfibrillated cellulose", Elsevier, Composites: Part A, 2014, vol. 59, pp. 26-29.

Lu et al., "Effects of modifications of bamboo cellulose fibers on the improved mechanical properties of cellulose reinforced poly(lactic acid) composites", Elsevier, Composites: Part B, 2014, vol. 62, pp. 191-197.

Pöllänen et al., "Cellulose reinforced high density polyethylene composites—Morphology, mechanical and thermal expansion properties", Elsevier, Composites Science and Technology, 2013, vol. 76, pp. 21-28.

Ranganathan et al., "Regenerated Cellulose Fibers as Impact Modifier in Long Jute Fiber Reinforced Polypropylene Composites: Effect on Mechanical Properties, Morphology, and Fiber Breakage", Journal of Applied Polymer Science, 2015, DOI: 10.1002/APP. 41301, pp. 1-10.

* cited by examiner

MODIFIED CELLULOSE AND COMPOSITE MATERIAL USING THE SAME

This application claims the benefit of Taiwan application Serial No. 103146047, filed Dec. 29, 2014, the disclosure of which is incorporated by reference herein in its entirety.

TECHNICAL FIELD

The disclosure relates in general to a cellulose and a composite material using the same, and more particularly to a modified cellulose and a composite material using the same.

BACKGROUND

Cellulose is the most abundant polymer in nature. In cellulose, each glucose unit includes three OH groups. Since most of OH groups may generate hydrogen bonds, cellulose forms stable crystal structure, and high bonding force may be formed between celluloses. Further, cellulose is a natural biomass material, and has a heat-resistant, high toughness and other advantages, so that it is widely used in composites.

However, general polyolefin polymers are oleophilic materials having low surface energy. The polyolefin polymers have low polarity, and the interface force between the polyolefin polymers and the hydrophilic plant fiber material are not easy to be formed. Therefore, it is not conducive to manufacturing the composite having cellulose for mechanical reinforcement.

SUMMARY

The disclosure is directed to a modified cellulose and a composite material using the same, which separates the cellulose crystal structure by cellulose activation technology, and then implements the surface modification to proceed a grafting reaction with the OH groups on the surface of the cellulose, such that the compatibility of the hydrophobic polymer may be increased and the cellulose material compatible with the petrochemical plastics such as polypropylene may be obtained. The disclosure may effectively solve the problems of the compatibility, processability and mechanical properties of the composite material formed with the biomass cellulose.

According to one embodiment, a modified cellulose is provided. The modified cellulose is represented by the chemical formula (1):

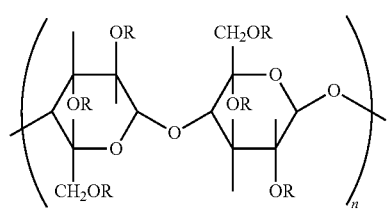

wherein n is between 60 and 2500, at least one R is selected from one of the group consisting of

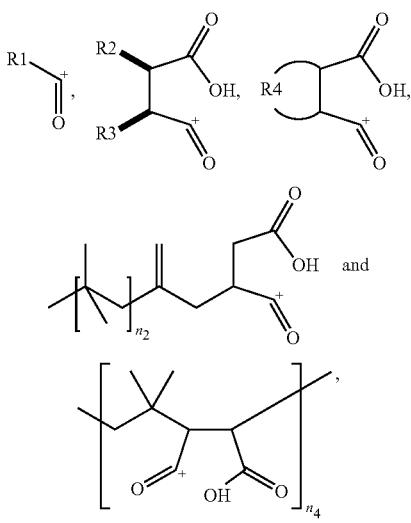

R1 is $C_{11}$ to $C_{32}$ alkyl group or $C_{11}$ to $C_{32}$ alkenyl group, R2 is hydrogen, $C_3$ to $C_{29}$ alkyl group or $C_3$ to $C_{29}$ alkenyl group, R3 is $C_3$ to $C_{29}$ alkyl group or $C_3$ to $C_{29}$ alkenyl group, R4 is $C_4$ to $C_8$ cycloalkyl group or $C_4$ to $C_9$ cycloalkenyl group, $n_2$ is between 15 and 33, $n_4$ is between 20 and 40.

According to another embodiment, a composite material including polypropene and a modified cellulose is provided. The modified cellulose is represented by the chemical formula (1):

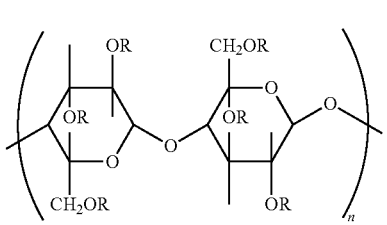

wherein n is between 60 and 2500, at least one R is selected from one of the group consisting of

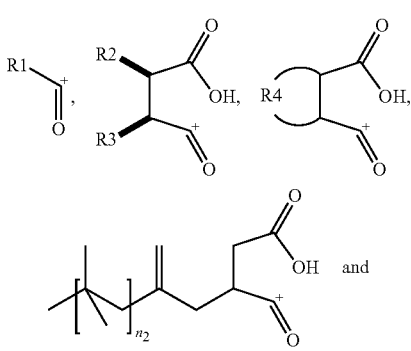

-continued

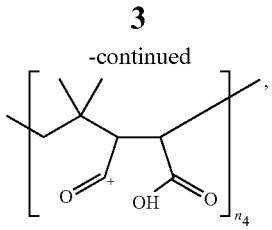

R1 is $C_{11}$ to $C_{32}$ alkyl group or $C_{11}$ to $C_{32}$ alkenyl group, R2 is hydrogen, $C_3$ to $C_{29}$ alkyl group or $C_3$ to $C_{29}$ alkenyl group, R3 is $C_3$ to $C_{29}$ alkyl group or $C_3$ to $C_{29}$ alkenyl group, R4 is $C_4$ to $C_8$ cycloalkyl group or $C_4$ to $C_8$ cycloalkenyl group, $n_2$ is between 15 and 33, $n_4$ is between 20 and 40.

BRIEF DESCRIPTION OF THE DRAWINGS (None)

In the following detailed description, for purposes of explanation, numerous specific details are set forth in order to provide a thorough understanding of the disclosed embodiments. It will be apparent, however, that one or more embodiments may be practiced without these specific details.

DETAILED DESCRIPTION

The embodiments are described in details. It is important to point out that some steps of the process in the embodiment according to the disclosure may be simplified or omitted for introducing the technical features more clearly, and there may be other embodiments of the present disclosure which are not specifically described. Thus, the specification is regarded as an illustrative sense rather than a restrictive sense.

The modified cellulose in the embodiment according to the disclosure may be represented by the chemical formula (1):

(1)

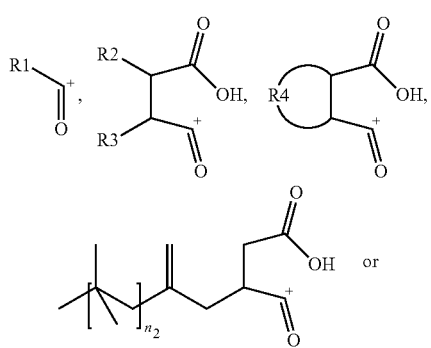

wherein n is between 60 and 2500, R may be hydrogen,

At least one R is selected from one of the group consisting of

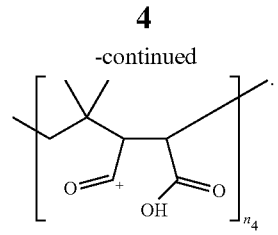

R1 is $C_{11}$ to $C_{32}$ alkyl group or $C_{11}$ to $C_{32}$ alkenyl group, R2 is hydrogen, $C_3$ to $C_{29}$ alkyl group or $C_3$ to $C_{29}$ alkenyl group, R3 is $C_3$ to $C_{29}$ alkyl group or $C_3$ to $C_{29}$ alkenyl group, R4 is $C_4$ to $C_8$ cycloalkyl group or $C_4$ to $C_8$ cycloalkenyl group, $n_2$ is between 15 and 33, $n_4$ is between 20 and 40.

In one embodiment, the

may include

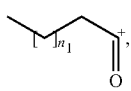

the

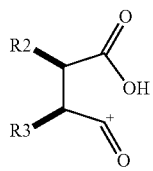

may include

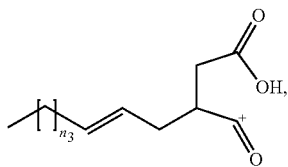

$n_1$ is between 9 and 15, and $n_3$ is 4 or 8.

The modified cellulose mentioned above may be formed by reacting a modification agent and a catalyst with a cellulose to carry out an esterification reaction. For example, the esterification reaction may be represented by the chemical equation (2):

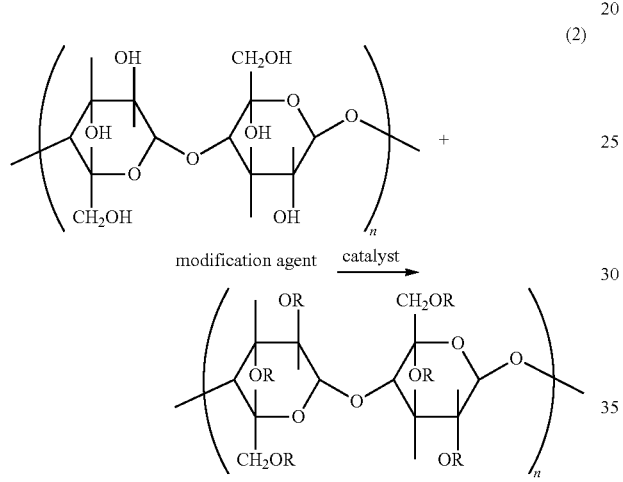

In one embodiment, the modification agent may include a material selected from the group consisting of wherein $n_1$ is between 9 and 15, $n_1'$ is between 9 and 15, $n_2$ is between 15 and 33, $n_3$ is 4 or 8, and $n_4$ is between 20 and 40. In other embodiments, the modification agent may include

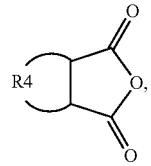

wherein R4 is $C_4$ to $C_8$ cycloalkyl group or $C_4$ to $C_8$ cycloalkenyl group, such as methylcyclohexene-1,2-dicarboxylic anhydride or methyl-5-norbornene-2,3-dicarboxylic anhydride Further, the catalyst may include a material selected from the group consisting of sulfuric acid, triethylamine and 4-dimethylaminopyridine.

In the embodiment according to the disclosure, the degree of substitution of the modified cellulose may be, for example, between 0.2 and 2.8. Here, the degree of substitution is defined as the average number of hydroxyl groups substituted by the reagents on each dehydration glucose unit in the cellulose molecule chain. Besides, the weight-average molecular weight of the modified cellulose synthesized by the reaction represented by the chemical equation (2) above may be such as between 10,000 and 400,000.

The following are the first example to the sixth example for describing synthesizing methods of the modified cellulose. The first to the sixth examples use different modification agents according to the disclosure to modify the cellulose. It should be noted that the synthesizing methods of the disclosure are not limited to any of the following embodiments. Any structure complying with the structures of the modification agents mentioned above may be used as the modification agent of the disclosure.

First Example

First, cellulose was soaked in pure water and stirred to a swelling state, and filtered and dried to obtain activated cellulose. 36 g of activated cellulose, 14.4 g of palmitic anhydride, 0.86 g of sulfuric acid and 395 g of acetic acid were taken into the reaction flask and heated to 85° C. for 5 hours. The product was poured into 480 mL of pure water, and stirred to be precipitated. Then, filtration, washing and drying were implemented to obtain the modified cellulose 1.

Second Example

First, cellulose was soaked in pure water and stirred to a swelling state, and filtered and dried to obtain activated cellulose. 20 g of activated cellulose, 15.12 g of polyisobutylene succinic anhydride (PIBSA), 9.92 g of triethylamine and 560 g of tetrahydrofuran (THF) were taken into the reaction flask and heated to 60° C. for 6 hours. The product was poured into hexane, and stirred to be precipitated. Then, filtration, washing and drying were implemented to obtain the modified cellulose 2.

Third Example

First, cellulose was soaked in pure water and stirred to a swelling state, and filtered and dried to obtain activated cellulose. 20 g of activated cellulose, 15.2 g of polyisobutylene maleic anhydride (PIBMA), 6.4 g of 4-dimethylaminopyridine (DMAP) and 560 g of dimethyl sulfoxide (DMSO) were taken into the reaction flask and heated to 80° C. for 6 hours. The product was poured into ethanol, and stirred to be precipitated. Then, filtration, washing and drying were implemented to obtain the modified cellulose 3.

Fourth Example

First, cellulose was soaked in pure water and stirred to a swelling state, and filtered and dried to obtain activated cellulose. 20 g of activated cellulose, 52.24 g of tetrapropenyl succinic anhydride, 19.8 g of triethylamine and 400 g of tetrahydrofuran (THF) were taken into the reaction flask and heated to 60° C. for 6 hours. The product was poured into hexane, and stirred to be precipitated. Then, filtration, washing and drying were implemented to obtain the modified cellulose 4.

Fifth Example

First, cellulose was soaked in pure water and stirred to a swelling state, and filtered and dried to obtain activated cellulose. 20 g of activated cellulose, 22.48 g of lauric anhydride, 11.96 g of 4-dimethylaminopyridine (DMAP) and 440 g of dimethyl sulfoxide (DMSO) were taken into the reaction flask and heated to 80° C. for 6 hours. The product was poured into ethanol, and stirred to be precipitated. Then, filtration, washing and drying were implemented to obtain the modified cellulose 5.

Sixth Example

First, cellulose was soaked in pure water and stirred to a swelling state, and filtered and dried to obtain activated cellulose. 20 g of activated cellulose, 16 g of methylcyclohexene-1,2-dicarboxylic anhydride, 11.96 g of 4-dimethylaminopyridine (DMAP) and 440 g of dimethyl sulfoxide (DMSO) were taken into the reaction flask and heated to 80° C. for 6 hours. The product was poured into pure water, and stirred to be precipitated. Then, filtration, washing and drying were implemented to obtain the modified cellulose 6.

TABLE 1 summarizes portion of the material characteristics of the modified celluloses in the first example to the sixth example.

TABLE 1

| | degree of substitution | weight-average molecular weight | pyrolysis temperature (° C.) |
|---|---|---|---|
| modified cellulose 1 | 0.94 | 100,000 | 305 |
| modified cellulose 2 | 2.01 | 136,000 | 333 |
| modified cellulose 3 | 2.20 | 145,000 | 344 |
| modified cellulose 4 | 2.20 | 172,000 | 256 |
| modified cellulose 5 | 1.50 | 98,000 | 342 |
| modified cellulose 6 | 2.20 | 145,000 | 340 |

TABLE 1 shows that the pyrolysis temperature of the modified cellulose obtained by the modification using the modification agents of the embodiments according to the disclosure may be higher than 300° C., which is suitable for mixing with polypropene (PP).

The composite material of the embodiment according to the disclosure may include polypropene and a modified cellulose represented by the chemical formula (1) above. In one embodiment, the content of the modified cellulose may be such as between 5 wt % and 50 wt %, and the weight-average molecular weight of the polypropene may be such as between 30,000 and 200,000.

Similarly, the modified cellulose may be formed by reacting a modification agent and a catalyst with a cellulose to carry out an esterification reaction. The modification agent may include a material selected from the group consisting of

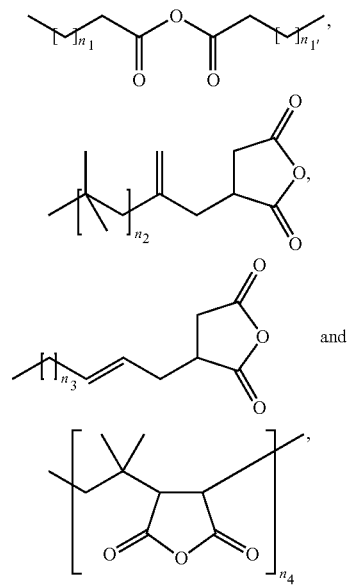

wherein $n_1$ is between 9 and 15, $n_1'$ is between 9 and 15, $n_2$ is between 15 and 33, $n_3$ is 4 or 8, and $n_4$ is between 20 and 40. In other embodiments, the modification agent may include

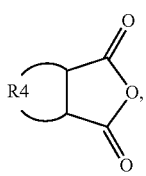

wherein R4 is $C_4$ to $C_8$ cycloalkyl group or $C_4$ to $C_8$ cycloalkenyl group, such as methylcyclohexene-1,2-dicarboxylic anhydride

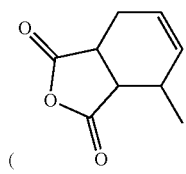

or methyl-5-norbornene-2,3-dicarboxylic anhydride

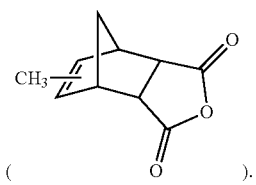

Further, the catalyst may include a material selected from the group consisting of sulfuric acid, triethylamine and 4-dimethylaminopyridine.

Then, the modified celluloses 1 to 6 synthesized in the first to the sixth examples were mixed with polypropene by the plastic spectrometer to form the composite material. The mixing temperature was 180° C., and the mixing time was set to be 5 minutes. The composite material which was completely mixed was cut to form ASTM specimen by vacuum thermal pressing for the flexural modulus test. Here, the flexural modulus was measured in accordance with ASTM D790 standard method.

Meanwhile, the first comparative example and the second comparative example were compared with composite material synthesized by the modified celluloses 1 to 6 in the first to the sixth examples.

The cellulose in the first comparative example was non-modified cellulose. The non-modified cellulose in the first comparative example was mixed with polypropene by the mass spectrometer. The mixing temperature was 180° C., and the mixing time was set to be 5 minutes. The specimen which was completely mixed was cut to form ASTM specimen by vacuum thermal pressing for the mechanical property test.

In the second comparative example, 20 g of oleic acid was dissolved in 110 g of toluene solvent to form modified solution. 5 g of plant fiber was immersed in the modified solution and heated to 130° C. for 5 hours. Then, the plant fiber was cleaned repeatedly by hexane to remove the unreacted oleic acid. The plant fiber was finally placed in an oven at 80° C. and dried to obtain surface-modified plant fiber. Since the surface-modified plant fiber had poor compatibility with polypropylene, the mixing process was not implemented.

TABLE 2 summarizes the results of the mechanical property test for the composite material formed by mixing different proportions of the modified celluloses in the first example to the sixth example with polypropene, the composite material formed by mixing the cellulose in the first comparative example with polypropene, and pure polypropene.

TABLE 2

| material | content of polypropene (wt %) | content of cellulose (wt %) | flexural modulus (kg/cm$^2$) |
|---|---|---|---|
| pure polypropene | 100 | 0 | 8291 |
| modified cellulose 1 + polypropene | 90 | 10 | 11707 |
| | 80 | 20 | 12547 |
| modified cellulose 2 + polypropene | 90 | 10 | 14925 |
| | 80 | 20 | 15329 |
| | 70 | 30 | 17076 |
| modified cellulose 3 + polypropene | 90 | 10 | 26032 |
| | 80 | 20 | 24884 |
| | 70 | 30 | 25201 |
| modified cellulose 4 + polypropene | 90 | 10 | 16324 |
| | 80 | 20 | 17144 |
| | 70 | 30 | 18076 |
| modified cellulose 5 + polypropene | 90 | 10 | 17828 |
| | 80 | 20 | 18741 |
| | 70 | 30 | 17230 |
| modified cellulose 6 + polypropene | 90 | 10 | 16870 |
| | 80 | 20 | 16751 |
| | 70 | 30 | 18200 |
| cellulose of first comparative example + polypropene | 90 | 10 | 9957 |
| | 80 | 20 | 11817 |

TABLE 2 shows that the composite materials formed by mixing the modified celluloses 1 to 6, which are modified by the modification agents according to the disclosure, with polypropene have better the mechanical properties than pure polypropene or the composite material formed by mixing the non-modified cellulose with polypropene.

According to the examples and the results of the experiments, the modified celluloses modified by the modification agents according to the disclosure have higher pyrolysis temperature. Further, the composite materials formed by mixing the modified celluloses modified by the modification agents according to the disclosure with polypropene have better the mechanical properties than pure polypropene or the composite material formed by mixing the non-modified cellulose with polypropene. The modified cellulose according to the disclosure may make the polypropylene have the properties of high heat resistance and high toughness, while keep the features of lightweight, environment protection and energy saving.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A modified cellulose, represented by the chemical formula (1):

(1)

[structure of cellulose repeating unit with OR, CH$_2$OR groups, subscript $n$]

wherein n is between 60 and 2500, R is hydrogen,

[structures showing R1–C(=O)–O⁺ group; R4-substituted cyclic group with COOH and CHO; long-chain structure with COOH, CHO and subscript $n_2$; and polymer unit with OH, two C=O groups and subscript $n_4$]

and at least one R is selected from one of the group consisting of

[same set of structures with "and" between them]

R1 is C$_{11}$ to C$_{32}$ alkyl group or C$_{11}$ to C$_{32}$ alkenyl group, R4 is C$_4$ to C$_8$ cycloalkyl group or C$_4$ to C$_8$ cycloalkenyl group, $n_2$ is between 15 and 33, $n_4$ is between 20 and 40.

2. The modified cellulose according to claim 1, wherein the

[structure R1–C(=O)–O⁺]

comprises

[structure with alkyl chain, subscript $n_1$, C=O]

and $n_1$ is between 9 and 15.

3. The modified cellulose according to claim 1, wherein a degree of substitution of the modified cellulose is between 0.2 and 2.8.

4. The modified cellulose according to claim 1, wherein the modified cellulose is formed by reacting a modification agent and a catalyst with a cellulose.

5. The modified cellulose according to claim 4, wherein the catalyst comprises a material selected from the group consisting of sulfuric acid, triethylamine and 4-dimethylaminopyridine.

6. The modified cellulose according to claim 4, wherein the modification agent comprises a material selected from the group consisting of palmitic anhydride, polyisobutylene succinic anhydride, polyisobutylene maleic anhydride, methylcyclohexene-1,2-dicarboxylic anhydride, methyl-5-norbornene-2,3-dicarboxylic anhydride and lauric anhydride.

7. The modified cellulose according to claim 1, wherein a weight-average molecular weight of the modified cellulose is between 10,000 and 400,000.

8. A composite material, comprising polypropene and a modified cellulose, the modified cellulose represented by the chemical formula (1):

(1)

[structure of cellulose repeating unit with OR, CH$_2$OR groups, subscript $n$]

wherein n is between 60 and 2500, R is hydrogen,

[structures showing R1–C(=O)–O⁺ group; R4-substituted cyclic group with COOH and CHO; long-chain structure with subscript $n_2$, COOH, CHO; polymer unit with OH, C=O groups and subscript $n_4$] or and at least one R is selected from one of the group consisting of

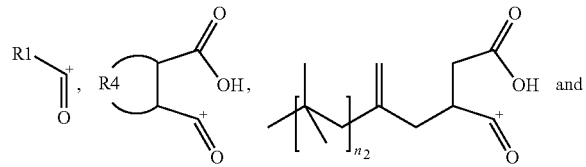

R1 is $C_{11}$ to $C_{32}$ alkyl group or $C_{11}$ to $C_{32}$ alkenyl group, R4 is $C_4$ to $C_8$ cycloalkyl group or $C_4$ to $C_8$ cycloalkenyl group, $n_2$ is between 15 and 33, $n_4$ is between 20 and 40.

9. The composite material according to claim 8, wherein the

comprises

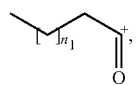

and $n_1$ is between 9 and 15.

10. The composite material according to claim 8, wherein a content of the modified cellulose is between 5 wt % and 50 wt %.

11. The composite material according to claim 8, wherein a degree of substitution of the modified cellulose is between 0.2 and 2.8.

12. The composite material according to claim 8, wherein the modified cellulose is formed by reacting a modification agent and a catalyst with a cellulose.

13. The composite material according to claim 12, wherein the catalyst comprises a material selected from the group consisting of sulfuric acid, triethylamine and 4-dimethylaminopyridine.

14. The composite material according to claim 12, wherein the modification agent comprises a material selected from the group consisting of palmitic anhydride, polyisobutylene succinic anhydride, polyisobutylene maleic anhydride, methylcyclohexene-1,2-dicarboxylic anhydride, methyl-5-norbornene-2,3-dicarboxylic anhydride and lauric anhydride.

15. The composite material according to claim 8, wherein a weight-average molecular weight of the modified cellulose is between 10,000 and 400,000.

16. The composite material according to claim 8, wherein a weight-average molecular weight of the polypropene is between 30,000 and 200,000.

* * * * *